United States Patent [19]

Hornby et al.

[11] 4,115,305

[45] Sep. 19, 1978

[54] SUPPORT MATRIX FOR CARRYING BIOLOGICALLY ACTIVE MATERIALS AND PROCESS FOR THE PREPARATION THEREOF

[75] Inventors: William Edward Hornby, Dairsie, Scotland; David Lindsey Morris, Guildford, England

[73] Assignee: National Research Development Corporation, London, England

[21] Appl. No.: 692,036

[22] Filed: Jun. 2, 1976

[30] Foreign Application Priority Data

Jun. 4, 1975 [GB] United Kingdom ............... 24125/75

[51] Int. Cl.$^2$ ............................................. C08L 89/00
[52] U.S. Cl. ......................................... 260/6; 195/63; 195/68; 195/DIG. 11; 260/9; 260/112 R
[58] Field of Search ................. 260/6, 112 R; 195/63, 195/68

[56] References Cited

U.S. PATENT DOCUMENTS

| | | | |
|---|---|---|---|
| 3,959,080 | 5/1976 | Orth | 195/63 |
| 3,969,287 | 7/1976 | Jaworek | 195/63 |
| 3,970,597 | 7/1976 | Sokolovsky | 195/63 |

FOREIGN PATENT DOCUMENTS 2,530,247  1/1976  Fed. Rep. of Germany.

OTHER PUBLICATIONS

Chem. Absts., vol. 83: 29416q, "Polymer Carriers for Biologically Active Materials", Hornby et al.

*Primary Examiner*—Edward M. Woodberry
*Attorney, Agent, or Firm*—Finnegan, Henderson, Farabow & Garrett

[57] ABSTRACT

A support for a biologically active material which comprises an organic polymer incorporating amidine groups the carbon atoms of which are bound to side chains each of which includes a functional group capable of linkage to a biologically active material, and a carbonyl group or an enol form thereof which is spaced from the carbon atom of an amidine group by the backbone dependent nitrogen atom thereof and at most by one other nitrogen atom in the side chain.

25 Claims, No Drawings

SUPPORT MATRIX FOR CARRYING BIOLOGICALLY ACTIVE MATERIALS AND PROCESS FOR THE PREPARATION THEREOF

This invention relates to polymeric supports for biologically active materials, and is an improvement in or modification of the invention described and claimed in British Patent Application No. 37230/73.

British Patent Application No. 37230/73 describes and claims an organic polymer suitable for use as a support for a biologically active material which comprises imidate groups capable of linkage to a biologically active material, and also a process for making such a polymer which comprises reacting a polymer comprising secondary amido and other groups to convert at least some of the amido groups to imidate groups without substantial cleavage of the polymer backbone. The imidate groups react with bisamines to give a support comprising a polymer containing amidine groups which has been found to show a marked tendency to bind protons when in contact with solutions at physiological pH values. This can be a disadvantage in certain situations, for example when the positively charged support carries a biologically active material for use as an immuno-adsorbent or for use in a continuous flow analysis apparatus. In both these applications, the positive charges on the support may interact with species present in the reaction medium leading to undesirable non-specific adsorption in the case of the immuno-adsorbents, and carry over of either reactants or products in the case of continuous flow analysers.

The present invention provides an organic polymer comprising amidine groups in which the tendency to bind a proton is relatively reduced, and a method for the production thereof.

According to the present invention, a support for a biologically active material comprises an organic polymer incorporating amidine groups the carbon atoms of which are bound to side chains each of which includes a functional group capable of linkage to a biologically active material, and a carbonyl group or an enol form thereof which is spaced from the carbon atom of an amidine group by the backbone dependent nitrogen atom thereof and at most by one other nitrogen atom in the side chain.

There is also included within the scope of the present invention a process for the production of a support for a biologically active material, in which imidate groups of an organic polymer are reacted with an organic compound so as to introduce into the polymer side chains which include a carbonyl group or an enol form thereof spaced from the polymer backbone by one or two nitrogen atoms of the side chain, and the side chains are then modified so as to comprise functional groups capable of linkage to a biiologically active material.

Organic polymers comprising imidate groups may be prepared by reacting polymers comprising primary or secondary amido groups with an alkylation reagent, by reacting polymers comprising amino-substituted aromatic groups with an ortho ester, or by subjecting polymers comprising nitrile groups to a condensation reaction with an alcohol in the presence of an acid. These methods are fully described in British Patent Application No. 37230/73. A preferred organic polymer for use in the production of the support of the present invention may be prepared by reacting nylon with an alkylation reagent such as for example a triethyloxonium salt.

In preferred supports according to the present invention the polymer backbone carries a side chain which includes a group A of formula $-N^1H-N^2H-CO-$ which may exist in a tautomeric form such as $=N^1-N^2H-CO-$, $-N^1H-N^2=C(OH)-$, or $=N^1-N^2=C(OH)-$, $N^1$ being the dependent nitrogen atom of an amidine group incorporated in the polymer. The group A is typically linked directly to the group $-R-CO-$, R representing an organic radical. Such supports the side chains of which comprise the group $-CO-R-CO-$, the acyl group corresponding to a dicarboxylic acid, may be produced by reaction of imidate groups in a polymer with compounds comprising an acid hydrazide group and in particular the alkyl and aryl hydrazides and dihydrazides, such as for example succinic acid dihydrazide, adipic acid dihydrazide, phthalic acid dihydrazide, dipicolinic acid dihydrazide, oxalic acid dihydrazide and dihydrazides derived from polysaccharides such as those hereinafter described. The product is then treated so as to provide the side chain with a suitably active functional group for linkage to a biologically active material, for example by modification of the free $-CONH\ NH_2$ groups in an acid dihydrazide side chain.

The reaction between a polymer comprising imidate groups and an acid hydrazide or dihydrazide may be carried out at ambient temperatures, in an inert organic solvent such as for example formamide, which does not significantly degrade the polymer backbone.

The hydrazide or dihydrazide is preferably sufficiently soluble to give a concentration in formamide at ambient of at least 50m. molar. Although the coupling reaction is preferably carried out in a predominantly non aqueous solvent, it may in some cases be carried out under aqueous conditions at temperatures below ambient, relatively higher pH values and relatively increased concentrations of hydrazide or dihydrazide.

The functional group capable of a linking reaction with a biologically active material may be an aldehyde group, which can be coupled to the biologically active material by a standard method such as the glutaraldehyde method or by a method described and claimed in British Patent Application Nos. 16148/73 and 37230/73, although other functional groups such as adipimidate, suberimidate, malonimidate and succinimidate may be used if so required. Reaction of imidate groups in the polymer with acid dihydrazides results in the production of an intermediate having side chains comprising an acid hydrazide group of which $-CO-NH-NH_2$ is readily convertible to an aldehyde group ($-CHO$) by oxidation under mild alkaline conditions. The group $-CO-NH-NH_2$ may alternatively be converted to an acid azide group ($-CON_3$) conveniently by reaction with sodium nitrite and hydrochloric acid, which azide group may be coupled directly to the biologically active material.

If desired the number of functional groups available for linkage to the biologically active material may be increased relative to the number of amidine groups in the polymer by selection of a side chain which is linked directly to a plurality of such functional groups. A compound comprising a plurality of reactive groups, for example, a polysaccharide or an oxidation product thereof may be reacted with an acid dihydrazide or hydrazine to produce a polyhydrazide or polydihydrazide which is linked by one of the plurality of free acid hydrazide groups on the polysaccharide or by way of an intermediate acid dihydrazide to the polymer backbone usually by reaction with an imidate group thereof. Pectin and oxidised dextran, especially periodate oxidised dextran, are particularly suitable.

Compounds comprising an acid hydrazide group are believed to react according to the following reaction scheme, as for example with the imidate ester of a nylon:

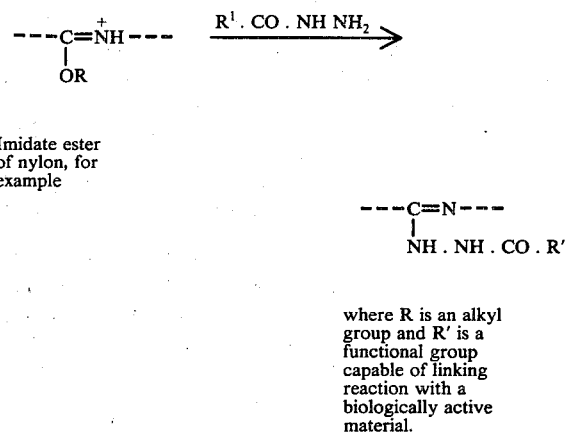

Imidate ester of nylon, for example where R is an alkyl group and R' is a functional group capable of linking reaction with a biologically active material.

Although the invention is not limited to any particular theory, it is believed that the amidrazone derivative shown above has a side chain which may tautomerise to produce a structure comprising double bonds in extended conjugation, i.e., that the structure I tautomerises to structure II:

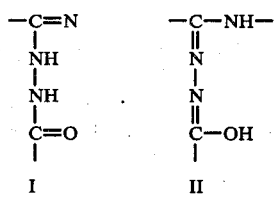

Structure II has carbon-nitrogen bonds in extended conjugation and is believed to protonate to a lower degree in aqueous media than structure I. It is believed that the latter tautomerism contributes to reducing the build up of localised positive charges on the support when in contact with aqueous media.

A wide range of biologically active materials and particularly proteins may be linked to the organic polymers of the present invention to produce biologically active matrices. These include enzymes present in or isolated from animal, plant or microbiological tissue such as for example, proteolytic enzymes such as trypsin, dhymotrypsin and pepsin; hydrolases such as β-galactosidase, ribonuclease, alkaline phosphatase, amyloglucosidase, dextranase, cholesterol esterase, urease, penicillinase and invertase; dehydrogenases such as lactic dehydrogenase, liver alcohol dehydrogenase, yeast alcohol dehydrogenase glucose dehydrogenase and glucose-6-phosphate dehydrogenase; kinases such as creatine phosphokinase, pyruvate kinase and hexokinase; oxidases such as peroxidase, glucose oxidase, cholesterol oxidase urease and catalase; transaminases such as glutamate-pyruvate transaminase and glutamate-oxalacetate transaminase; and amidases such as penicillin amidase.

Alternatively, the biologically active material may be a co-factor such as, for example, nicotinamide adenine dinucleotide (NAD), nicotinamide adenine dinucleotide phosphate (NADP) and their reduced forms, adenosine diphosphate ribose (ADP-ribose), adenosine triphosphate (ATP), adenosine diphosphate (ADP), adenosine monophosphate (AMP), pyridoxamine phosphate, pyridoxal phosphate, a pterin, a flavin, or co-enzyme A; an inhibitor such as, for example, an organophosphorous compound; or an antigen or antibody.

The linking reaction in which the biologically active material is covalently bound to the organic polymer is preferably carried out under very mild conditions. Alkaline conditions are preferred, and the most favourable pH at which to bind the biologically active material to the organic polymer is the highest pH which the biologically active material in solution can tolerate without losing its activity. Usually the pH is within the range of from 7 to 10, and preferably from 7.5 to 9. Binding is conveniently carried out in phosphate buffer but the choice of phosphate as a coupling buffer is not obligatory. Buffers which do not contain free primary amino groups can be used e.g. N-ethylmorpholine, imidazole, ethylenediaminotetraacetic acid. Buffers such as TRIS are not recommended however as the free amino groups in these compounds will react with the activated nylon. The amount of biologically active material bound to the organic polymer per unit weight of polymer, and the specific activity of the bound biologically active material can be maximised by controlling the pH of the reaction medium, the time of reaction, and the ratio of biologically active material to organic polymer in the reaction mixture. An adequate time of reaction is usually between about 15 minutes and 1 hour.

The invention is illustrated by the following Examples:

EXAMPLES 1–4

A nylon tube is filled with a 10% by weight solution of triethyloxonium tetrafluoroborate in dichloromethane and the O-alkylation reaction allowed to proceed for 15 minutes to produce an imidate salt of the nylon tube. After washing with dichloromethane to remove any traces of unreacted alkylation reagent, the tube is cut into one meter lengths which are filled with either a) a 140 mM solution of adipic acid dihydrazide in formamide or b) a 140 mM solution of succinic acid dihydrazide in formamide, and the reaction allowed to proceed for one hour at room temperature. The tubes are then washed exhaustively with distilled water, and activated either (i) by filling the tube with a solution of diethyl adipimidate (30 mg ml$^{-1}$) in 20% (v/v) N-ethylmorpholine in methanol, incubating for 40 minutes at room temperature and then washing with methanol, or (ii) by perfusing with a 5% (w/v) solution of glutaraldehyde in 0.2M - borate buffer, pH 8.5 for 15 minutes at room temperature and then washing free of excess glutaraldehyde by perfusion for 5 minutes. with 0.1M - phosphate buffer pH 8.0.

Finally each tube is filled with a 1 mg/ml aqueous solution of rabbit muscle lactate dehydrogenase in a neutral phosphate buffer and incubated for 2 to 3 hours at 40° C.

The amounts of enzyme immobilised and the activities of the nylon tube supported enzymes are given in the Table 1.

TABLE

| Example | Procedure | Nylon-Tube Derivative | Enzyme immobilised (mg $M^{-1}$) | Tube Activity (moles $M^{-1} min^{-1}$) |
| --- | --- | --- | --- | --- |
| 1 | (a) (i) | Adipic acid dihydrazide - adipimidate-enzyme | 0.56 | 0.37 |
| 2 | (b) (i) | Succinic acid dihydrazide - adipimidate-enzyme | 0.56 | 0.19 |
| 3 | (a) (ii) | Adipic acid dihydrazide -glutaraldehyde-enzyme | 0.25 | 0.61 |
| 4 | (b) (ii) | succinic acid dihydrazide - glutaraldehyde-enzyme | 0.22 | 0.52 |

Derivatives of glucose oxidase, catalase and lactate dehydrogenase are prepared in a similar fashion and, for comparison, derivatives of the same enzymes are prepared using 1,6 — diaminohexane in place of the acid dihydrazide. It is found that when used in a continuous flow analyser the acid dihydrazide derivatives have considerably improved carry-over characteristics by comparison with the diamine derivatives. For example, the lactate dehydrogenase dihydrazide derivative reveals considerably less carry-over due to pyridine nucleotide binding then the corresponding diamine derivative. It is found that dihydrazide derivatives can be used at a sample rate of 70 samples/hour with acceptable carry-over, whereas the diamine derivatives can only be used satisfactorily up to a sample rate of 40 samples/hour.

EXAMPLE 5

A. Preparation of Polymer: Nylon tube (Type 6 nylon 0.1 cm bore) is alkylated by filling it with a 12% (w/v) solution in dichloromethane of triethyloxonium tetrafluoroborate and incubating at 25° C for 15 minutes. The tube is then washed free of excess alkylating agent by perfusion for 1 minute with dichloromethane at a flow rate of 20 ml/minute.

B. Preparation of Succinic Acid Hydrazide: A 4% (w/v) solution of the hydrazide in formamide is prepared by suspending with stirring 4g. succinic acid hydrazide in 100 ml formamide at 55° C and stirring for 10 minutes when a solution is obtained.

C. Coupling of Hydrazide to Polymer: The alkylated nylon tube (imidate salt of nylon) is filled with a solution of the hydrazide and incubated for 2 hours at 25° C. Thereafter excess hydrazide is removed by washing through with 5 liters of water overnight at 25° C.

D. Activation of Support for Enzyme Binding: The hydrazide-substituted nylon tube is activated for enzyme binding with glutaraldehyde by filling the tube with a 5% (w/v) solution of glutaralydehyde in 0.2M-borate buffer, pH 8.5, and incubating for 10 minutes at 25° C. Excess glutaraldehyde is removed by washing through with 0.1 M-phosphate buffer, pH 7.0 for 3 minutes at a flow rate of 10 ml/minute. The tube is used immediately thereafter for binding enzyme.

E. Enzyme Binding: The tube is filled with a solution of the enzyme (0.2-2.0 mg $ml^{-1}$) in 0.1M-phosphate buffer, pH 7.5, and incubated for 3 hours at 4° C. Thereafter excess enzyme and physically-bound enzyme is removed by perfusing the tube with 500 ml 0.5M-NaCl 25° C, at a flow rate of 10 ml/minute.

EXAMPLE 6

The procedure of Example 5 is repeated with the substitution of oxalic acid hydrazide for succinic acid hydrazide.

EXAMPLE 7

The procedure of Example 5 is repeated with the substitution of adipic acid hydrazide for succinic acid hydrazide.

EXAMPLE 8

The procedure of Example 5 is repeated with the substitution for succinic acid hydrazide of a polyfunctional acid hydrazide derived from pectin by the following procedure:

Pectin (polygalacturonic acid methyl ester) from citrus fruits reacts with hydrazine to form the acid hydrazide derivative. 10g pectin is suspended in 100 ml methanol and 25 ml hydrazine hydrate is added. The mixture is stirred at 30° C for 36 hours. Thereafter excess hydrazine is removed by washing the product in 80% (v/v) methanol in water as follows. The pectin-hydrazide is suspended with stirring in 250 ml methanol-$H_2O$ for 30 minutes after which the product is collected by filtration on a Buchner funnel. This process is repeated six times. The product is finally washed in ether and dried at room temperature.

The acid hydrazide derivative of pectin is prepared for use as follows. 1g. of the derivative is dissolved in 25 ml 0.1M-$NaHCO_3$, pH 9.5, by stirring at 35° C for 1 hour. The resulting solution is used for reaction with the imidate salt of the nylon.

EXAMPLE 9

The procedure of Example 5 is repeated with the substitution for succinic acid hydrazide of a polyfunctional acid hydrazide derived from dextran by the following procedure: Dextran from Leuconostoc mesenteroides (MW 100-200,000) is first oxidatively cleaved with periodate. 10g dextran are dissolved with stirring in 200 ml water and the solution is titrated to pH 6.0. 6g sodium metaperiodate ($NaIO_4$) is added over a period of 2 hours, the mixture is stirred throughout at 4° C and kept in a dark bottle. The pH is maintained at 6.0 throughout. The solution is left overnight at 4° C. Excess periodate is removed by dialysis against running tap water for 5 hours. The solution of periodate-oxidised dextran is titrated to pH 7.5 with 1.0M-NaOH and 25 g. adipic acid hydrazide is added. The mixture is stirred for 3 hours at room temperature, and maintained at pH 7.5 throughout. Excess hydrazide is removed by dialysis against running tap water for 6 hours. The hydrazide-derivatised dextran is freeze dried and stored in the lyophilised state. The acid hydrazide is prepared for use as described in Example 8.

EXAMPLES 10-14

The procedures respectively of Examples 5-9 are repeated with the substitution of the following procedure for step D:

The tube is filled with a solution of either diethyladipimidate or dimethylsubermidate (5% (w/v) in 20% (v/v) N-ethylomorpholine in anhydrous methanol) and incubated for 2 hours at 25° C. Excess imidate is removed by washing through with methanol for 2 minutes at a flow rate of 10 ml/min. The tube is used immediately thereafter for binding enzyme.

EXAMPLES 15–19

The procedures respectively of Examples 5–9 are repeated with the substitution of the following procedure for step D:

The tube is perfused in a closed loop with 100 ml ice-cold 1.0M-HCl. 1.0g. $NaNO_2$ is added to the residual acid in the reservoir over a period of 5 minutes and the pumping is continued for a further 5 minutes at a flow rate of 10 ml/min. The tube and the acid reservoir must be maintained at 0° C throughout. Excess nitrous acid is then removed by washing through with ice-cold 1mM-HCl for 2 minutes at a flow rate of 10 ml/min. The tube is used immediately thereafter for binding enzyme.

EXAMPLES 20 and 21

The procedure of Examples 7 and 12 are repeated, the support being activated in the latter Example with diethyladipimidate. The enzyme aldehyde dehydrogenase (ALDH) is then bound to the support as described in Example 5 (step E).

In order to assess carry over, tubes supporting ALDH are prepared as described in Example 5 step A with 1,6-diaminohexane following which the support is coupled to ALDH in one case by adipimidate and in another by glutaraldehyde.

The four tubes are thus:
(i) Nylon - 1,6-diaminohexane - glutaraldehyde - ALDH
(ii) Nylon - 1,6-diaminohexane - adipimidate - ALDH
(iii) Nylon - adipic acid hydrazide - glutaraldehyde - ALDH
(iv) Nylon - adipic acid hydrazide - Adipimidate - ALDH Each of the tubes is incorporated in turn in a system composed of Standard Technicon AA1 modules. Reduced nicotinamide adenine dinucleotide (NADH) is sampled at the rate of 60 samples/hour with a 2:1 (v/v) sample: wash ratio at a flow rate of 0.23 ml/minute into a stream comprising air at a flow rate 0.60 ml/minute and 0.1M phosphte buffer, pH 7.5 at a flow rate 2.50 ml/minute. The liquid stream is passed through a small mixing coil at 25° C and then through the nylon tube at 25° C following which the NADH is analysed by a spectrophotometer (340nm.). The rate of the flow directed to waste after passing through the spectrophotometer is 2.00 ml/minute carryover is evaluated by peak height analysis of the spectrophotometric peaks obtained from 3 NADH Samples (1.0mM) followed by 3 NADH Samples of lower concentration (0.2 mM). The carryover coefficients K for the four tubes are as follows:

K
(i) 0.0405
(ii) 0.0890
(iii) 0.0143
(iv) 0.0143

These results show that those derivatives prepared with hydrazide spacers display relatively diminished carryover.

We claim:

1. A biologically active matrix comprising a support and a biologically active material which is bound thereto, said support comprising an organic polymer incorporating amidine groups the carbon atoms of which are bound to side chains each of which includes a functional group capable of linkage to the biologically active material, and a carbonyl group or an enol form thereof which is spaced from the carbon atom of an amidine group by the backbone dependent nitrogen atom thereof and at most by one other nitrogen atom in the side chain.

2. A matrix according to claim 1, in which the polymer is a modified nylon.

3. A matrix according to claim 1, in which the side chains include a group A which exists in one or more of the tautomeric forms $-N^1HN^2HCO-$, $=N^1-N^2HCO$, $-N^1H-N^2=C(OH)-$, and $=N^1-N^2=C(OH)-$, $N^1$ representing the dependent nitrogen atom of an amidine group incorporated in the polymer.

4. A matrix according to claim 3, in which said group A is directly linked to the group —R—CO—, R representing an organic radical.

5. A matrix according to claim 4, in which side chains include the group —CORCO— which represents succinyl, oxalyl, adipoyl, phthaloyl or dipicolinoyl.

6. A matrix according to claim 1, in which the side chain comprises a polysaccharide carrying a plurality of functional groups capable of linkage to the biologically active material.

7. A matrix according to claim 6, in which the polysaccharide is linked to the carbon atoms of the amidine groups by the group —A—R—CO—NH—NH— in which R represents an organic radical.

8. A matrix according to claim 6, in which the polysaccharide is an oxidised dextran.

9. A matrix according to claim 3, in which the side chain comprises a polysaccharide which carries a plurality of functional groups capable of linkage to the biologically active material and which is linked to the carbon atoms of the amidine groups in the polymer by the group A.

10. A matrix according to claim 9, in which the polysaccharide is pectin.

11. A matrix according to claim 1, in which said functional groups are aldehyde, azide, adipimidate, suberimidate or glutaraldehyde groups.

12. A matrix according to claim 1, in which the biologically active material is a protein.

13. A matrix according to claim 12, in which the biologically active material is an enzyme, a co-factor, inhibitor, antigen or antibody.

14. An intermediate for the production of a support for a biologically active material which comprises an organic polymer incorporating amidine groups the carbon atoms of which are bound to side chains comprising an acid dihydrazide which includes the backbone dependent nitrogen atom of the amidine groups.

15. An intermediate according to claim 14, in which the polymer is a modified nylon.

16. An intermediate according to claim 14, in which the dihydrazide is of a succinic acid, oxalic acid, adipic acid, phthalic acid or dipicolinic acid.

17. An intermediate according to claim 14, in which the side chain comprises a hydrazide of oxidised dextran or pectin.

18. A process for the production of a support for a biologically active material in which imidate groups of an organic polymer are reacted with an organic compound so as to introduce into the polymer side chains which include a carbonyl group or an enol form thereof spaced from the polymer backbone by one or two nitrogen atoms of the side chain, and the side chains are then modified so as to comprise functional groups capable of linkage to a biologically active material.

19. A process according to claim 18, in which the polymer is a modified nylon.

20. A process according to claim 18, in which the organic compound is an acid dihydrazide.

21. A process according to claim 20 in which the dihydrazide is a succinic, oxalic, adipic, phthalic or dipicolinic acid.

22. A process according to claim 20, in which the organic compound comprises a polysaccharide.

23. A process according to claim 18, in which the reaction is carried out in an at least predominantly non aqueous solvent at a compound concentration at least 50mM.

24. A process according to claim 18, in which the side chains are modified by conversion of a $-CONHNH_2$ group therein to an azide group.

25. A process according to claim 18, in which the side chains are modified by reaction of a $-CO\ NH\ NH_2$ group therein with glutaraldehyde, adipimidate or suberimidate.

* * * * *